United States Patent [19]

Thompson

[11] 4,286,589
[45] Sep. 1, 1981

[54] EXTENSION LEAD FOR A RESPIRATOR ALARM SYSTEM

[76] Inventor: Harris A. Thompson, 175 Bellevue Dr., Boulder, Colo. 80302

[21] Appl. No.: 93,795

[22] Filed: Nov. 13, 1979

[51] Int. Cl.³ ............................................. A61M 16/00
[52] U.S. Cl. ............................ 128/202.22; 128/205.23; 340/573
[58] Field of Search ...................... 128/202.22, 204.21, 128/204.22, 205.18, 30, 30.2, 7.6, 205.23, 204.23; 340/573, 512

[56] References Cited
U.S. PATENT DOCUMENTS

| 3,120,843 | 2/1964 | Hyman | 128/202.22 |
| 3,634,885 | 1/1972 | Barkley | 340/573 |
| 3,781,843 | 12/1973 | Harrison et al. | 340/573 |
| 3,840,006 | 10/1974 | Buck et al. | 128/202.22 X |
| 3,866,204 | 2/1975 | Barkley | 340/573 X |

Primary Examiner—Henry J. Recla
Attorney, Agent, or Firm—Frank C. Lowe; Jerry W. Berkstresser

[57] ABSTRACT

In an artificial respiration apparatus, especially in positive pressure types, it has been found that an extension lead for a respirator alarm system is desirable. This lead will extend beyond the respirator to permit a patient to initiate an alarm when help is needed. The lead is connected to the alarm initiating circuit in the respirator in a manner which makes its connection or disconnection optional with the alarm system in the respirator working in its regular manner when the extension lead is disconnected.

3 Claims, 3 Drawing Figures

EXTENSION LEAD FOR A RESPIRATOR ALARM SYSTEM

The present invention relates to alarm circuits in artificial respiration apparatus, and more particularly to an alarm circuit which may include a lead extending to the patient.

The invention is especially needed in positive pressure respiration apparatus. These respirators have been developed to aid a patient having breathing difficulties and a number of the respirators are for patients who are able to move around and are not confined to an artificial lung. Several different types are available. For example, fixed bellows and piston type respirators may be used in hospitals while portable blower types are used elsewhere. All of these respirators are mechanical in their operation and essentially all of them are driven by electricity, usually from a 110 volt A.C. power source supplemented by emergency storage batteries. Also, portable respirator units are available which operate with a storage battery when a patient is travelling and away from the 110 volt A.C. source.

Naturally, there is the possibility of breakdowns in the respirator machinery from a number of causes. For example, the unit may quit from a failure at the power source, a failure of the pumping machinery, the wearing out of motor brushes and the like. When continuous operation of a respirator can mean the difference between life and death for the patient, it becomes essential that some sort of warning or alarm system be incorporated into the respirator to let others know of a failure, or impending failure of operation so that timely action may be taken. Therefore, alarms of various sorts have been installed in respirators, such as a horn, a warning light on the respirator or even a light on a switchboard when the respirator is in a permanent installation.

The alarm devices associated with respiratory apparatus do not directly concern the patient. However, a patient may need to summon help or even faint or collapse and create an emergency as serious as a breakdown of the respirator. This can be serious if a hospital patient is using a respirator away from his bed and cannot reach the regular nurse calling signal at the bed.

The present invention was conceived and developed with the foregoing and other considerations in view and the invention comprises, in essence, a lead which may be connected into an alarm system of a respirator. Such a lead will include a switch at its terminal which, when actuated, will set off an alarm in the respirator. The switch may be a simple push-button type, or may have any one of several actuating aids so that an unusual movement of the patient can actuate it.

The objects of the present invention are thus, to provide a new and improved alarm extension lead for a respirator which: (a) may be connected to the respirator for use by a patient who cannot reach the respirator; (b) will not disturb any circuits in the respirator except for the provision of a connecting socket in the alarm trigger circuit; (c) is especially adapted for connection with the alarm trigger circuit in a manner which is essentially fool-proof and will not interrupt the normal operation of the trigger circuit within the respirator; (d) is a simple, low-cost item which can be used in a number of different types of respirators having alarms.

With the foregoing and other objects in view, the present invention comprises certain constructions, connections and circuit arrangements as hereinafter described, defined in the appended claims and illustrated in preferred embodiment in the accompanying drawings in which:

Figure 1:
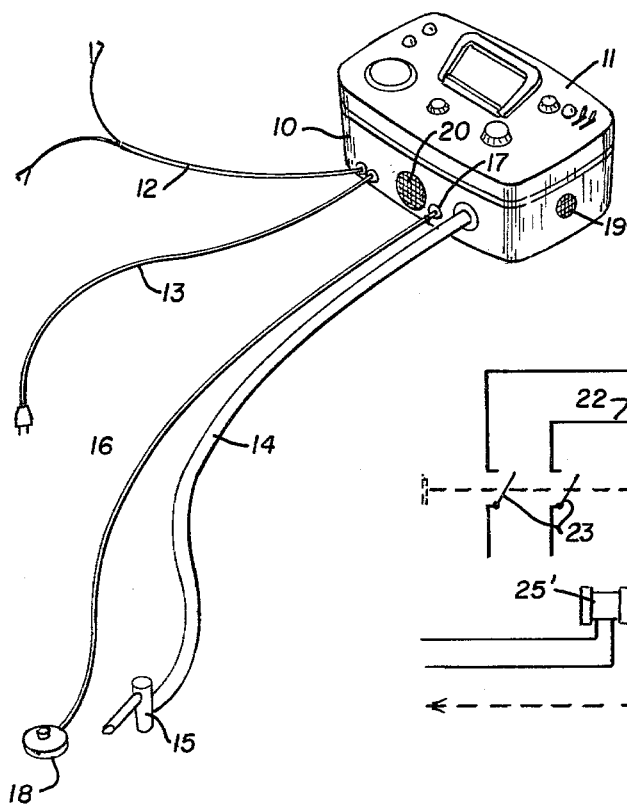
FIG. 1 is an isometric view of a respirator unit showing a breathing tube, electrical leads, and the alarm extension lead which can extend to a patient.

Referring more particularly to the drawing, a portable positive pressure respiration apparatus is ordinarily carried in a case 10 which is closed by a lid 11. The necessary controls and pressure and light indicators are located on the lid 11 although in some models, one or more control knobs may be located at a side of the case. The components outside this case include an electrical cord 12 for connection with a battery and a second electrical cord 13 for connection with a 110 volt A.C. supply source. A breathing tube 14 extends from the case with a mouthpiece 15 at its terminal end. In accordance with the present invention, an alarm extension lead 16 is connected to the case at a receptacle 17 provided for it and includes a switch 18 at its remote end as hereinafter further described.

Some of the components within the case, which are not shown since they are conventional, include a transformer and a rectifier to reduce the 110 volt A.C. current to a 12 volt D.C. current, the same as that produced by the storage battery. Also, a blower, driven by the electrical motor within it, provides a continuous airflow to the breathing tube 14 during inspiration by a patient and through exhaust ports 19 during expiration by the patient. Such cyclic breathing action is regulated by a cyclic valve associated with the blower.

These components, and the associated electrical circuits, can get out of order, the battery can become discharged, the brushes of an electrical motor can wear out, and any of these factors can stop the respirator, or cause it to perform improperly. Accordingly, a warning system, an alarm, is incorporated into most units. One type of alarm is a small horn carried in the case adjacent to an opening 20 where the sound can be easily heard. Such a horn will be energized by an independent circuit with its own battery so it will not have to rely on the regular power sources. This independent circuit will be activated by a voltage drop in a loop of the regular operative circuit of the respirator. A power failure will thus disrupt the voltage in this loop and various electrical or mechanical failures can cause relay switches on the loop to open as will now be described.

Figure 2:
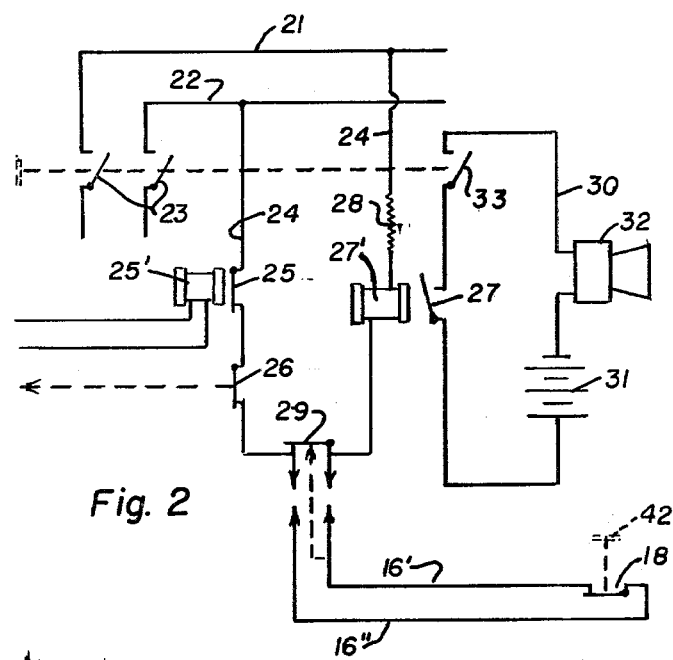
FIG. 2 is a circuit diagram of an alarm circuit, an alarm trigger circuit found within the respirator, and portions of operative circuits extending to the alarm trigger circuit.

Referring to FIG. 2, a fragment of the primary circuit leads 21 and 22 of the respirator are shown. These leads are energized by a double pole main switch 23. These primary leads are shunted by an alarm initiating loop 24 having a normally closed relay switch 25, a normally closed mechanical switch 26, a relay coil 27, and a suitable resistance 28 to minimize the current flow through this normally closed circuit. In addition, the initiating loop includes a normally closed switch 29 at the jack receptacle 17, as hereinafter described.

A warning circuit 30 alongside this loop 24 includes a battery 31, a horn 32, a main switch 33, which is mechanically linked to the main switch 23 to open and close in unison with that switch, and a normally open relay switch 27. The normal state of operation, when the main switches 23 and 33 are closed, is to energize relay coil 27', to hold switch 27 open and inactivate the warning circuit 30. Should an electrical event occur to energize relay coil 25' to open switch 25, or should a mechanical event occur to open switch 26, the coil 27' is deenergized, the switch 27 is closed and the alarm horn 32 commences sounding.

It is to be noted that several relay switches, such as switch 25, may be in series in the alarm initiator circuit 24 and the relay coils of such switches may be energized to hold the switches shut or to open them. Such relay coils, as may be necessary, will be associated with various electrical circuit components in the respirator and they will be energized or deenergized to open their switches whenever their associated components malfunction. There may also be several mechanical switches in the circuit 24 such as switch 26, and these switches, if used, will be associated with mechanical components to open whenever the mechanical components malfunction. Details of such various electrical circuit components and mechanical components will vary on different types of respirator machines. They are conventional and thus, need not be described further.

To incorporate an alarm extension lead 16 in this initiating circuit 24, it is necessary that the electrical loop forming the extension lead be incorporated into the circuit in series, and that the circuit 24 be opened at the point of connection, and normally closed switch 29 at the jack receptacle 17 will be opened.

Figure 3:
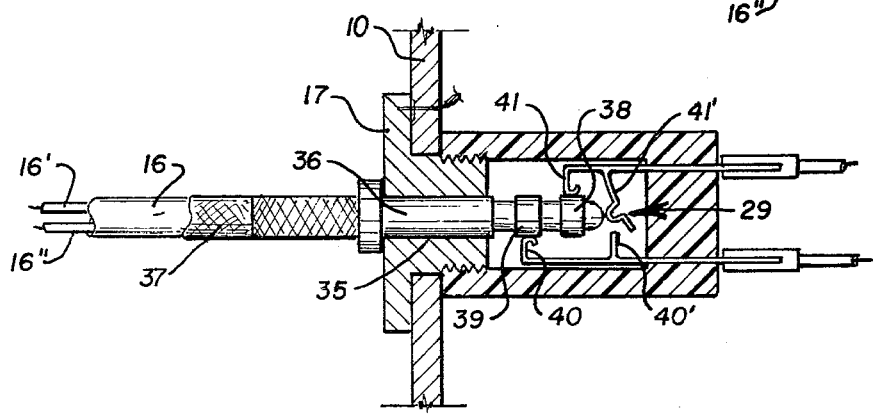
FIG. 3 is a diagrammatic sectional view of a jack receptacle construction which may be used with the present invention.

Referring to FIG. 3, this jack receptacle will include a socketed boss 35 in the wall of the case 10 to receive a cylindrical jack plug 36. The boss 35 may be grounded and the outer sleeve of the plug 36 is also a ground. A ground wire or a woven mesh 37 may be extended to the switch 18 of the lead 16. The plug 36 has a double connector end, an outward collar 38 connecting with one wire 16' of the extension lead, and an inward collar 39 connecting with the other wire 16" of the extension lead. These connectors, insulated from each other, are positioned to engage contact bars within the receptacle.

A first contact bar 40 at one side of the initiating circuit 24 engages the collar 39 and a second contact bar 41 engages the collar 38. Each contact bar 40 and 41 has a finger 40' and 41', respectively, which are engaged when the jack plug is not in the receptacle 17 and they hold the circuit 24 closed when so engaged. When the jack plug 36 is in the receptacle, however, the end 38 pushes against the finger 41' to separate these fingers 40' and 41 and open the circuit 24.

The swtich 18 at the end of the lead 16 is a normally closed switch and opens when a button 42 or the like is pressed. The switch 18 is not shown in detail because it can take several forms, from a simple push button type to an elaborate pressure responsive unit where it is arranged to open the circuit should a patient faint and fall upon it. These variations, matters of design, will all function properly with a normally closed switch and when this switch opens, an alarm will be sounded. The convenience of this arrangement is first that it is essentially foolproof, and secondly, that when the alarm extension is removed, the alarm circuit in the respirator will function in a conventional manner, switch 29 being again closed.

I have now described my invention in considerable detail. However, it is obvious that others skilled in the art can build and devise alternate and equivalent constructions and circuit arrangements which are within the spirit and scope of the invention. Hence, I desire that my protection be limited, not by the constructions described, but only by the proper scope of the appended claims.

What is claimed is:

1. In a respirator having: a primary circuit energized by an electrical power source to drive the respirator components; a normally closed alarm-initiator circuit connecting with the primary circuit; means associated with the respirator components to open the alarm-initiator circuit whenever a respirator component fails or the power source fails; a normally open alarm circuit having an alarm means and an independent power source to actuate the alarm means whenever the circuit closes; and means associated with the alarm-initiator circuit to close the alarm circuit whenever the alarm-initiator circuit opens, the improvement comprising:

a disconnectable extension lead extended from the respirator, having a normally-closed, manually-actuatable switch at its extended end adapted to provide a manually actuated alarm function by the patient opening the normally closed manually-actuatable switch, and means in the alarm-initiator circuit adapted to close the circuit at the respirator connection point of the extension lead when disconnection of the extension lead is made, to maintain the alarm-initiator circuit in a closed state, and to open the circuit at the point of connection when connection of the extension lead is made, to place the lead in series with the alarm-initiator circuit.

2. The organization defined in claim 1 wherein the extension lead is connected to a plug having two contact points, one for each end of the lead wire, and the connection point at the respirator is a socket having two contact points, one for each side of the alarm-initiator circuit and being adapted to engage the plug contact points when the plug is inserted into the socket, and a switch means in the alarm-initiator circuit at the socket adapted to normally close the circuit across the contact points but to open whenever the plug is inserted into the socket.

3. The organization defined in claim 2 wherein said switch means is positioned in the socket to be engaged and opened by the plug when it is inserted in the socket.

* * * * *